(12) United States Patent
Takii et al.

(10) Patent No.: US 8,298,832 B2
(45) Date of Patent: Oct. 30, 2012

(54) METHOD OF AGITATING SOLUTION

(75) Inventors: Yuki Takii, Kamakura (JP); Kunihisa Nagino, Moriyama (JP); Fumio Nakamura, Tokyo (JP); Hitoshi Nobumasa, Otsu (JP)

(73) Assignee: Toray Industries, Inc. (JP)

( * ) Notice: Subject to any disclaimer, the term of this patent is extended or adjusted under 35 U.S.C. 154(b) by 844 days.

(21) Appl. No.: 10/593,680

(22) PCT Filed: Mar. 17, 2005

(86) PCT No.: PCT/JP2005/004746
§ 371 (c)(1),
(2), (4) Date: Oct. 17, 2006

(87) PCT Pub. No.: WO2005/090997
PCT Pub. Date: Sep. 29, 2005

(65) Prior Publication Data
US 2007/0178603 A1 Aug. 2, 2007

(30) Foreign Application Priority Data

Mar. 23, 2004 (JP) ................................. 2004-084318

(51) Int. Cl.
*G01N 1/00* (2006.01)
*C12Q 1/00* (2006.01)
*C12Q 1/68* (2006.01)
*B01F 11/00* (2006.01)
(52) U.S. Cl. .............. 436/174; 435/4; 435/6.1; 366/241
(58) Field of Classification Search ................... 436/174
See application file for complete search history.

(56) References Cited

U.S. PATENT DOCUMENTS

| 4,815,978 | A | * | 3/1989 | Mazza et al. ..................... 435/4 |
| 5,770,461 | A | * | 6/1998 | Sakazume et al. ............ 436/526 |
| 5,780,306 | A | * | 7/1998 | Schels et al. .................. 436/179 |
| 5,807,522 | A | | 9/1998 | Brown et al. |
| 7,476,313 | B2 | * | 1/2009 | Siddiqi ......................... 210/222 |
| 2003/0134316 | A1 | * | 7/2003 | Tashiro et al. .................... 435/6 |

FOREIGN PATENT DOCUMENTS

| JP | 10-503841 T | 4/1998 |
| JP | 2001-108683 A | 4/2001 |
| JP | 2003-248008 A | 9/2003 |
| JP | 2003-329679 A | 11/2003 |
| JP | 2003-339375 A | 12/2003 |
| JP | 2004-20386 A | 1/2004 |
| JP | 2004-144521 A | 5/2004 |
| JP | 2004-264289 A | 9/2004 |
| JP | 2004-357698 A | 12/2004 |

* cited by examiner

*Primary Examiner* — Sam P Siefke
*Assistant Examiner* — Bryan Kilpatrick
(74) *Attorney, Agent, or Firm* — DLA Piper LLP (US)

(57) ABSTRACT

The method of stirring a solution according to the present invention is a method of stirring a solution comprising contacting a selective binding substance immobilized on the surface of a carrier with a solution containing an analyte substance reactive with the selective binding substance, and mixing the fine particles or air bubbles into the solution containing an analyte substance, and moving the fine particles or air bubbles without allowing contact thereof with the selective binding substance-immobilized surface.

The present invention provides a stirring method that accelerates the reaction of a carrier-immobilized selective binding substance with an analyte substance and detects a trace amount of analyte at high signal intensity and high S/N ratio. The present invention enables diagnosis and examination in the clinical setting by using a selective binding substance-immobilized carrier such as DNA chip.

9 Claims, 6 Drawing Sheets

METHOD OF AGITATING SOLUTION

TECHNICAL FIELD

The present invention relates to a method of stirring a solution containing an analyte substance, when a carrier-immobilized selective binding substance is allowed to react with an analyte substance by bringing a carrier carrying an immobilized substance selectively binding to an analyte substance ("selective binding substance" in the present description) into contact with a solution containing an analyte substance. More specifically, it relates to a method of stirring a solution containing an analyte substance for acceleration of the reaction between a carrier-immobilized selective binding substance and the analyte substance.

BACKGROUND ART

Research for analysis of genetic information of various organisms is now under progress. A great number of genes including those of human, the base sequences thereof, proteins coded by the gene sequences, and sugar chains produced secondary from these proteins are now being elucidated quite rapidly. The functions of the genes, proteins, and sugar chains with known sequence can be studied by various methods. Nucleic acids, and their relationship with various genes and biological functions, can be studied by using various nucleic acid/nucleic acid complementarity, for example by Northern or Southern blotting. The function and expression of proteins can be studied by using protein/protein reactions, for example by western blotting.

A new analytical method called DNA-microarray method (DNA chip method) was developed recently as a method of analyzing expression of multiple genes simultaneously and is attracting attention. These methods are in principle the same as conventional methods in that they are the nucleic acid detecting and quantitative determining method based on nucleic acid/nucleic acid hybridization reaction. These methods are applicable to the methods of detecting and quantitatively determining proteins and sugar chains, based on specific protein/protein, sugar chain/sugar chain, or sugar chain/protein interaction. These methods are characteristic in that a planar glass substrate called microarray or DNA chip carrying multiple DNA fragments, proteins, and sugar chains immobilized thereon orderly at high density is used. Typical examples of the DNA chip method includes a method of hybridizing, for example, an expression gene in the cell under investigation with a fluorescent dye-labeled sample on a planar substrate, allowing complementary nucleic acids (DNA or RNA) to bind to each other, and scanning the reaction sites with a high-definition detection device (scanner) at high speed, and a method of detecting a response, for example in electric current, based on electrochemical reaction. In this manner, it is possible to estimate the amount of a particular gene in sample rapidly. Application of the DNA chip is not limited to gene expression analysis of estimating the amount of expressed gene, and it is highly expected as a means to detect single nucleotide polymorphism (SNP).

For example, a method of coating a flat substrate such as slide glass with poly-L-lysine, aminosilane, or the like and immobilizing nucleic acids by using a spotting device called spotter was developed as a method of immobilizing a nucleic acid on substrate (Published Japanese Patent Application No. 10-503841).

cDNAs and the fragments thereof having hundreds to thousands of bases, which were used traditionally as the nucleic acid probe (nucleic acid immobilized on substrate) for use in DNA chip, are being replaced gradually by oligo DNAs (oligo DNAs are DNAs having a base number of 10 to 100), because oligo DNAs reduce the error during hybridization with analyte and are easily prepared in synthesizer. The oligo DNAs are bound to the glass plate covalently (Published Japanese Patent Application No. 2001-108683).

Currently, DNA chips are mainly used as a research tool for analyzing a great number of genes at once by placing from tens of thousands of to several thousand of genes on a single chip. It is hoped that DNA chips will be used more widely in diagnostic applications. Generally when the DNA chip is used in diagnostic application, it is predicted that the amount of the sample collected would be very small. Current DNA chips are still insufficient in sensitivity, and thus, it would be impossible to analyze such a sample. In addition, with a current DNA chip, the fluorescence intensity of genes lower in expression amount after hybridization is very low, and thus, the current DNA chips still have a problem that it is practically impossible to analyze such genes. Accordingly, current DNA chips have a problem that how to increase the fluorescent intensity after hybridization of the samples lower in quantity and genes lower in expression amount. To solve the problem above, it is critical to improve the efficiency of the reaction between the analyte DNA and the probe DNA. For acceleration of the reaction between analyte DNA and probe, natural diffusion of the analyte is insufficient, and it is thought that accelerating the reaction between probe and analyte efficiently by stirring the solution.

For example as a method of stirring an analyte solution, Published Japanese Patent Application Nos. 2003-248008 and 2003-339375 disclose a method of increasing the reaction efficiency with an analyte by agitating an analyte solution while moving magnetic beads in the analyte solution by magnetic force. Alternatively, Published Japanese Patent Application No. 2003-339375 discloses a method of increasing the signal after hybridization, by bringing an analyte solution containing beads into contact with a DNA chip, sealing the solution, for example, with a cover glass, forcing the beads to drop in the gravitational direction while rotating the chip, and thus agitating the analyte solution.

However, the methods described in Published Japanese Patent Application Nos. 2003-248008 and 2003-339375 still had the following problems.

That is, generally when an analyte solution is sealed with a common cover glass on a flat plate-shaped DNA chip, the clearance between the cover glass and the DNA chip is approximately 10 μm at most. Thus, it caused a problem that fine particles larger in diameter than the clearance, when added, are held in the clearance between the DNA chip and the cover, prohibiting movement of the fine particles and making the stirring ineffective. In addition, use of fine particles of several μm in diameter, caused a problem that the fine particles do not move in the analyte solution efficiently because of the solution resistance even if forced by gravity or the like, resulting in insufficient stirring. Contact of the fine particles with the DNA probe-immobilized carrier seems to be one reason for insufficient characteristic of stirring even the migration of the fine particles is forced by gravity. Alternatively, the solution may be stirred by agitating the fine particles in the reaction solution, by expanding the clearance between the cover glass and the DNA chip for example with an O-ring, increasing the size of the agitating fine particles, and forcing the movement of the particles by gravitational or magnetic force. However, the cover glass and the DNA chip are both flat in shape for sealing, and thus, the fine particles move through the DNA probe-immobilized region. As a result, the fine particles often damaged the probe DNA-immobilized region, causing problems such as difficulty of data analysis and decrease in signal intensity because of separation of the probe by collision of the fine particles to the probe-immobilized surface.

DISCLOSURE OF THE INVENTION

The present invention provides a method of stirring a solution comprising contacting a selective binding substance immobilized on the surface of a carrier with a solution containing an analyte substance reactive with the selective binding substance, and mixing the fine particles or air bubbles into the solution containing an analyte substance, and moving the fine particles or air bubbles without allowing contact thereof with the selective binding substance-immobilized surface.

EXPLANATION OF REFERENCES

Figure 1:
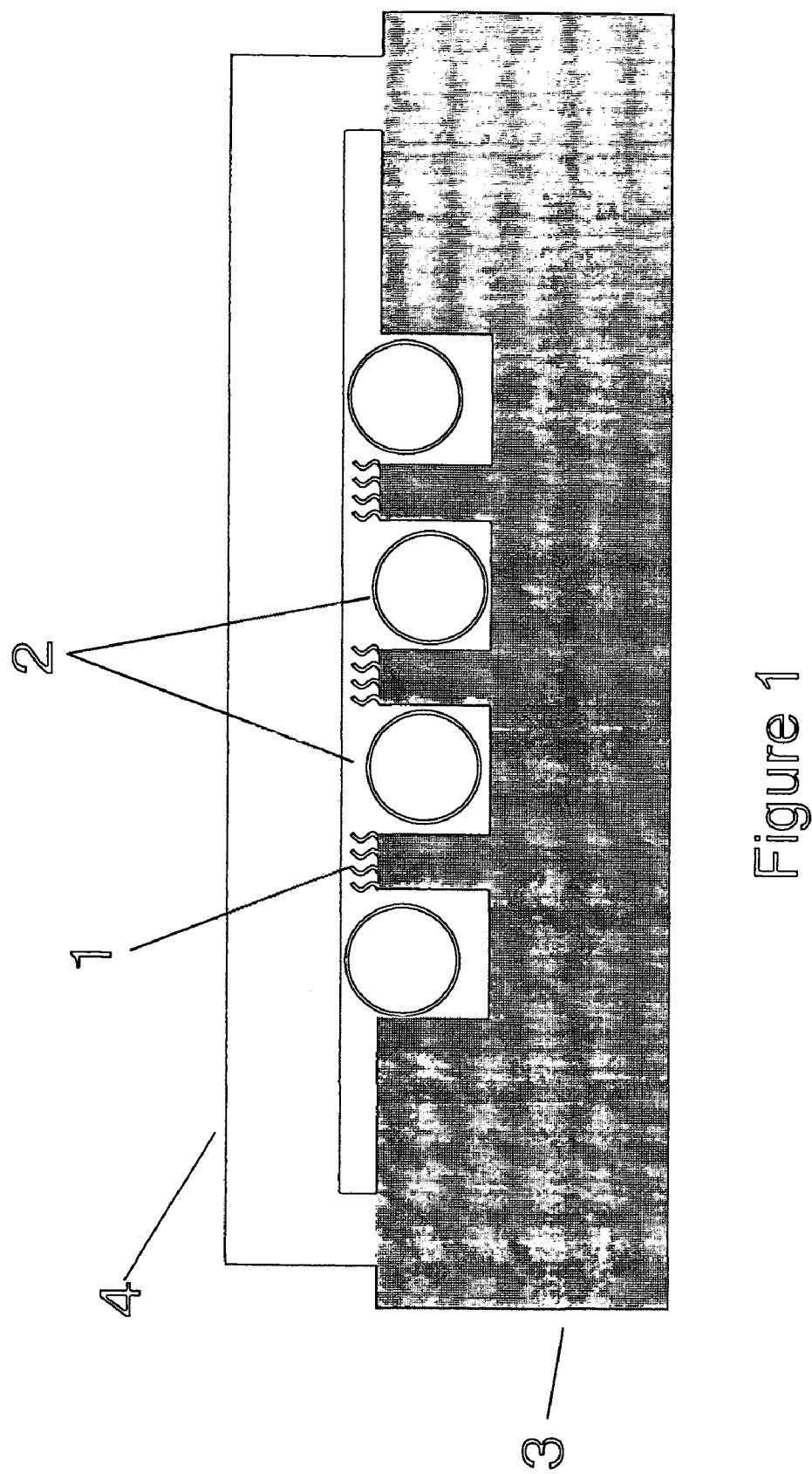
FIG. 1 is cross-sectional schematic view of an embodiment of the present invention.

| | |
|---|---|
| 1 | Carrier-immobilized selective binding substance (DNA) |
| 2 | Fine particles (beads) |
| 3 | Carrier |
| 4 | Reaction container for solution |
| 11 | Flat area |
| 12 | Convex-concave area |
| 13 | DNA chip |
| 14 | Object lens |
| 15 | Laser excitation light |
| 16 | Spring for fixing microarray to jig |
| 31 | Selective binding substance-immobilized layer |
| 32 | Support layer |
| 41 | PMMA |
| 42 | DNA |
| 51 | Magnet |
| 52 | Direction of magnet reciprocating motion |
| 53 | Substrate |

BEST MODE FOR CARRYING OUT THE INVENTION

Hereinafter, the method of stirring a solution according to the present invention will be described.

The first method of stirring a solution according to the present invention is a method of comprising contacting a selective binding substance immobilized on the surface of a carrier with a solution containing an analyte substance reactive with the selective binding substance, mixing fine particles or air bubbles into the solution containing an analyte substance, and moving the fine particles or air bubbles without allowing contact thereof with the selective binding substance-immobilized surface.

In the first method of stirring a solution according to the present invention, the solution should be stirred by mixing the fine particles or air bubbles into the solution containing an analyte substance and moving the fine particles or air bubbles.

Also in the first method of stirring a solution according to the present invention, the solution is stirred by moving the fine particles or air bubbles without allowing contact thereof with the selective binding substance-immobilized surface. It becomes possible to prevent damage on the surface caused by contact of the fine particles or air bubbles with the probe-immobilized surface, by restricting the movable range of the fine particles or air bubbles.

It is preferable to use a carrier in such a structure that the fine particles or air bubbles do not become in contact with the selective binding substance-immobilized surface. Preferably, the carrier has convex-concave surface, and the selective binding substance is immobilized on the top face of the convexes.

It is also preferable to use a container holding a solution in such a structure that the fine particles or air bubbles do not become in contact with the selective binding substance-immobilized surface.

The second method of stirring a solution according to the present invention is a method of stirring a solution comprising contacting a selective binding substance immobilized on the top face of convexes of a carrier with a solution containing an analyte substance reactive with the selective binding substance, mixing fine particles or air bubbles into the solution containing the analyte substance, and moving the fine particles or air bubbles.

Air bubbles or fine particles are used in the first and second methods of stirring a solution according to the present invention. When air bubbles and fine particles are compared, use of fine particles is preferable both in the first and second methods of stirring a solution according to the present invention, because it is possible to control the density easily by selecting the size and kind of the material.

In the method of stirring a solution according to the present invention, the size of the fine particles (maximum diameter of fine particles) is preferably 10 μm or more. When a size of the fine particles is smaller than 10 μm, there is the case that most of the effects by stirring with fine particles may not be provided. It is because when a size of fine particles is smaller than 10 μm, there is the case the fine particles may not almost move, even if an external field (magnetic field, gravity, or vibration) is applied, because of the resistance of the solution. The size of the fine particles is particularly preferably 20 μm or more.

Fine particles in any shape may be used in the method of stirring a solution according to the present invention. The fine particle is particularly preferably spherical, i.e., bead-shaped. Favorably, when the fine particle is bead-shaped, the particles move smoothly in the reaction solution without stagnation by their own rotation, consequently allowing favorable stirring of the analyte solution. The fine particles are most preferably spherical fine particles (beads) having a diameter of 20 to 300 μm. When the bead diameter is in the range above, the beads migrate easily by gravity or acceleration in the solution because of the weight thereof even if there is resistance by the reaction solution, making the solution stirred sufficiently, and thus, use of such beads gives a favorable result.

In the method of stirring a solution according to the present invention, the material for the fine particles is not particularly limited. Examples of the materials for fine particles include metals, glass, ceramics, and polymers (such as polystyrene, polypropylene, and nylon). Among them, beads of a material higher in density than water (such as glass, quartz, or zirconia ceramic) are preferable, because the beads migrate easily in solution assisted by acceleration by gravity or vibration. Alternatively, magnetic beads may also be used. In particular, beads of zirconia ceramic are higher in density and most preferable, because they migrate easily by acceleration by gravity or vibration. Alternatively, glass, quartz, and zirconia ceramics are also favorable, because smaller amounts of bead components are dissolved and released into the analyte solution.

Beads of a zirconia ceramic (yttria-stabilized zirconia) are particularly favorable, because the beads have a density of 6 $g/cm^3$, higher than that of quartz glass at 2.2 $g/cm^3$, and are thus higher in stirring efficiency; and allow easier handling, because they are resistant to disturbance, for example when a solution containing them is placed in a container and shaken for sealing.

In the method of stirring a solution according to the present invention, the solution is stirred preferably by moving fine particles. More preferably in the method of stirring a solution according to the present invention, the fine particles are forced to move by gravity, magnetic force, or vibration of carrier, or by combination thereof. Among them, a method of moving beads by gravity while rotating the carrier along a vertical face is preferable, because the method is easier to perform and gives a sufficiently advantageous effect. The rotational velocity then is preferably 0.1 to 30 rpm. When a rotational velocity is more than 30 rpm, there is the case that gravity may be applied to fine particle in the opposite direction, before it moves completely in one direction. As a result, the distance of the reciprocal movement of the fine particles in the analyte solution shortens, there is the case that the enough effect of the stirring may not be shown. Alternatively when a rotational velocity is less than 0.1 rpm, there is the case that the total period may shorten when the fine particles are moving in solution, consequently the period of stirring the analyte solution may shorten and there is the case that the enough effect may not be shown. For that reason, the preferable range of rotational velocity is 0.5 to 5 rpm. In a favorable method, fine particles in solution are agitated, with additional acceleration by horizontal vibration of the carrier.

In the method of stirring a solution according to the present invention, a container for solution is used preferably. More preferably in the method of stirring a solution according to the present invention, the solution is stirred by movement of fine particles and the minimum width of the fine particles is greater than the minimum distance between the selective binding substance-immobilized surface and the container for solution.

Preferably in the method of stirring a solution according to the present invention, the maximum width of the fine particles is 10 µm or more and less than the difference in height between the top face of convexes and the concave area.

Preferably in the method of stirring a solution according to the present invention, the solution is stirred by movement of fine particles and the carrier has convex-concave surface, and the selective binding substance is immobilized on the top face of convexes and the fine particles move in the concave area.

Preferably in the method of stirring a solution according to the present invention, the carrier has a flat area and a convex-concave area, the selective binding substance is immobilized on the top face of the convexes, the height of the top face of the convexes is almost the same, and the difference in height between the flat area and the top face of the convexes is 50 µm or less.

Hereinafter, favorable shapes of the carrier on which the selective binding substance is immobilized will be described below.

Preferably, the selective binding substance-immobilized carrier for use in the stirring method according to the present invention has a convex-concave area, and the selective compatible substance is immobilized on the top face of the convexes. It is possible to obtain favorable results such as low noise and higher S/N ratio by using a carrier in such a structure, because there is no analyte non-specifically adsorbed thereon that is observed during detection. Specifically, the reason for low noise is as follows: When a carrier having a selective binding substance immobilized on the top face of the convexes is scanned in a device called scanner, because the laser beam is focused on the top face of the convexes in the convex-concave area, the laser beam is defocused in concave area, preventing the undesirable fluorescence (noise) of the analyte non-specifically adsorbed in concave area.

As for the height of the convex in the convex-concave area, the top faces thereof preferably have almost the same height. The height almost the same described above means a height that does not cause any significant difference in fluorescence intensity level when a fluorescent labeled analyte is allowed to react with a selective binding substance immobilized on the surfaces of convexes slightly different in height and the bound analytes on respective surfaces are scanned with a scanner. Concretely, the height almost the same mean a difference in height of 50 µm or less. The difference in height is more preferably 30 µm or less; and still more preferably, the height is the same. The same height in this patent application includes the errors due to the fluctuations that may occur during production or the like. When a difference in height between the highest top face of the convexes and the lowest top face of the convexes is greater than 50 µm, laser beam on the top faces of the convexes different in height may blur, and consequently, signal intensity from the analyte bound in reaction with the selective binding substance immobilized on the top face of the convexes may weaken.

The top face of the convex is preferably, substantially flat. The term "substantially flat" means that the convex top face does not have an irregularity of 20 µm or more in height.

The carrier for use in the stirring method according to the present invention preferably has a flat area. The height of the convex top faces in the convex-concave area and the height of the flat area are preferably, almost the same. That is, the difference in height between the flat area and the convex top face is preferably less than 50 µm or less. When a difference in height between the convex top face and the flat area is 50 µm or more, detectable fluorescence intensity may weaken. The difference in height between the flat area and the convex top face is more preferably 30 µm or less; and most preferably, the height of the flat area and the height of the convex are the same as each other.

Figure 3:
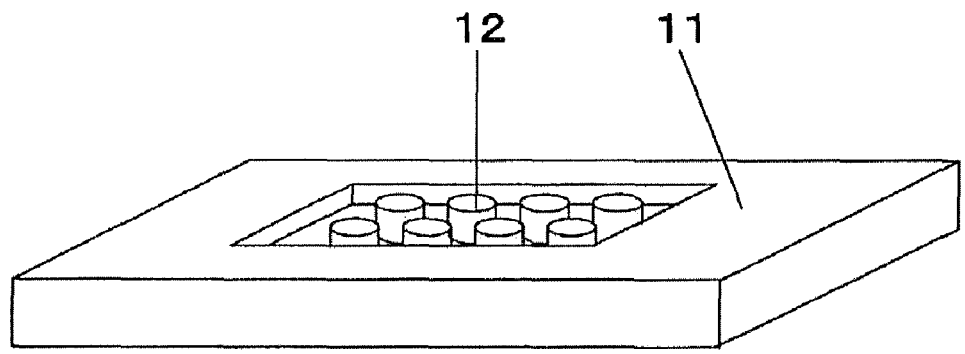
FIG. 3 is a schematic view illustrating a carrier.
Figure 4:
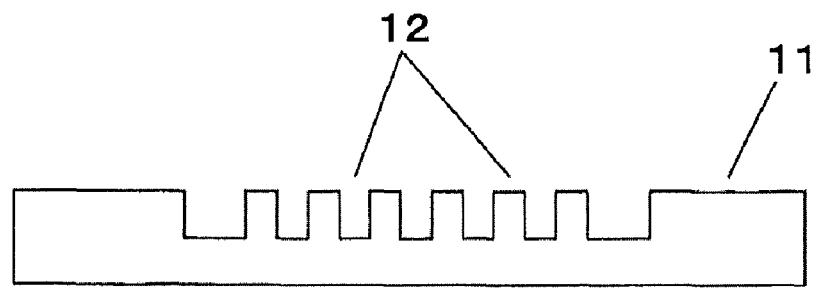
FIG. 4 is a cross-sectional schematic view illustrating a carrier.
Figure 5:
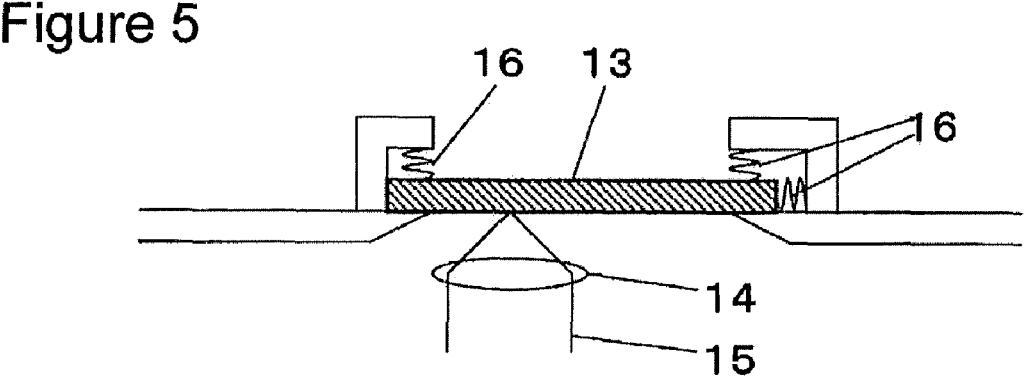
FIG. 5 shows an example of a DNA chip-fixing jig.

Typical examples of the carriers for use in the stirring method according to the present invention are shown in FIGS. 3 and 4. There is a flat area indicated by 11 around a convex-concave area, and a selective binding substance (e.g., nucleic acid) is immobilized on the top face of the convexes indicated by 12 in the convex-concave area. It is possible to focus the scanner excitation light on the top face easily by using the flat area. Often for focusing the excitation light of a scanner on the carrier surface, the carrier is fixed to a jig as shown in FIG. 5, and the focal point of the laser beam is previously adjusted in height to the surface of the jig. It is thus possible to focus the scanner laser beam on the top face of the convexes on the carrier easily, by pressing the flat area of the carrier used in the stirring method according to the present invention to the surface of the jig.

In the method of stirring a solution according to the present invention, the multiple selective binding substance-immobilized convexes on the carrier on which the selective binding substance is immobilized means the region on which a selective binding substance (e.g., nucleic acid) essential for data acquisition is immobilized, and the region on which only a dummy selective binding substance is immobilized is not included.

In the method of stirring a solution according to the present invention, the carrier on which the selective binding substance is immobilized preferably has the convexes having the almost same area of the top face. When the areas of the convex top faces are almost the same, the multiple regions on which the selective binding substance is immobilized have almost the same area, which is advantageous in the later analysis. The phrase "the areas of the respective top faces of convexes are preferably almost the same" means the value of the largest top face area divided by the smallest top face area of all the convexes is 1.2 or less.

In the method of stirring solution according to the present invention, the area of the convex top face on the carrier on which the selective binding substance is immobilized is not particularly limited, but is preferably 1 mm$^2$ or less and 10 μm$^2$ or more, for reduction of the amount of the selective binding substance used and from the point of easiness in handling.

In the method of stirring a solution according to the present invention, the height of the convexes in the convex-concave area of the carrier favorably used is preferably 10 μm or more and 500 μm or less. For the reason described below, it is particularly preferably 50 μm or more and 300 μm or less. When a convex height is lower than the value above, the nonspecifically adsorbed analyte sample in the area other than the spots may be dietected and consequently S/N ratio may become deteriorated. When a convex height is 500 μm or more, it may cause problems such as easier cracking and breakage of the convex.

In the first method of stirring a solution according to the present invention, the movement range of the fine particles or air bubbles is restricted. Typical shape of the container holding the carrier and the solution for that purpose will be described with reference to FIG. 1.

In FIG. 1, reference numeral 1 denotes a probe DNA (selective binding substance). Reference numeral 2 denotes fine particles (beads in this case), and reference numeral 3 denotes a probe DNA-immobilized carrier. Those components denoted by reference numerals 1, 2, and 3 become in contact with a solution containing a target DNA (analyte substance). Reference numeral 4 denotes a container holding liquid, for example made of a material such as slide glass, cover glass, metal, or plastic, and the target DNA-containing solution is held between the container and the carrier. In the example of FIG. 1, the probe DNA is immobilized on the convexes of the carrier. The minimum distance between the top face of the convexes on carrier (selective binding substance-immobilized face) and the solution-containing container is smaller than the diameter of the fine particles, preventing contact of the fine particles with the probe DNA-immobilized face and damage of the face by the fine particles. When the fine particles are, for example, elliptical in shape, and when the minimum distance between the top face of the convexes and the container is smaller than the minimum width of the fine particles, it is possible to prevent contact of the probe-immobilized face with the fine particles.

A condition to realize the situation of FIG. 1 concretely is placing a solution containing an analyte DNA (analyte solution) dropwise on a carrier which has convex-concave structure, adding fine particles into the solution while preventing deposition thereof on the top face of the convexes, covering it with a cover glass equivalent to container, and sealing the cover glass, for example, with an adhesive tape or agent for prevention of spill or vaporization of the analyte solution. In this way, there is formed a space containing the analyte solution having a thickness of from several to dozens of μm between the cover glass face and the top face of the convexes. When the size of the fine particles is greater than the distance between the cover glass face and the top face of the convexes, the fine particles do not damage the top face of the convexes. It is possible to guide the fine particles to pass through only the concave area in the convex-concave area and stir the analyte solution without the fine particles becoming in contact with the top face of the convexes, for example, by using a carrier in such a shape and rotating the carrier in a vertical plane. Preferably to form the space containing an analyte solution between the top face of the convexes and the container reliably, for example, a plate having the corners on the plate face higher by 5 to 100 μl than the other face or a plate having its central area lowered by 5 to 100 μm is used, and the plate is connected to the selective binding substance-immobilized carrier with the central area of the plate facing the convex-concave area of the carrier. An example of the plate is shown in FIG. 1(4). Such a container can be prepared, for example, by treating glass with hydrofluoric acid, bonding a film or adhesive tape at 2 to 4 corners of a flat plate, preparing a plate having the shape shown in FIG. 1(4), for example by injection molding, or forming raised dots at the corners of a plate by screen printing.

In the method of stirring a solution according to the present invention, a container holding solution in such a structure that the fine particles or air bubbles do not become in contact with the selective binding substance-immobilized surface is preferably used.

Figure 2:
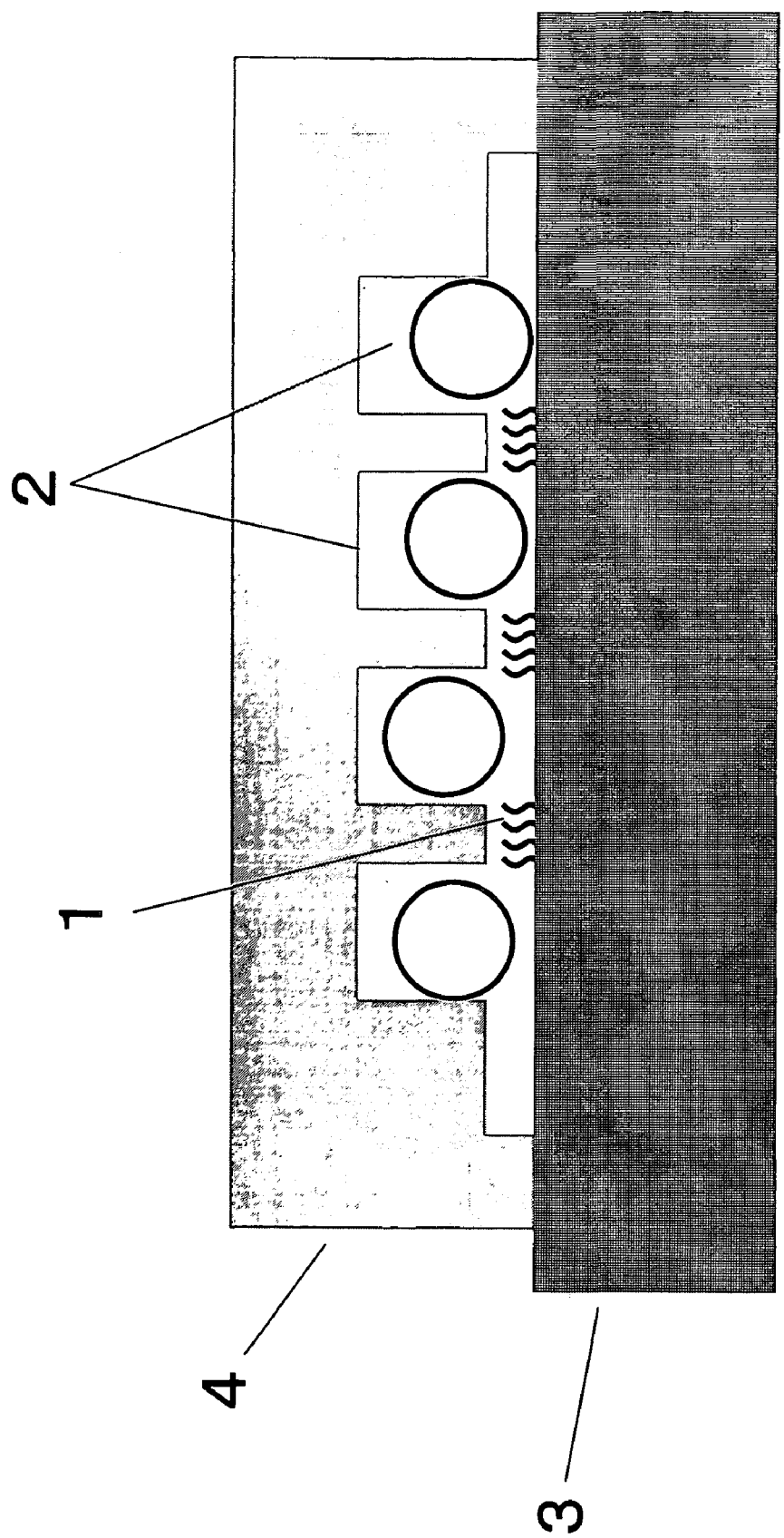
FIG. 2 is cross-sectional schematic view of another embodiment of the present invention.

The carrier in FIG. 1 has convex-concave shape. It is also possible to obtain a similar effect by forming convex-concave structure on the container for solution. A typical example thereof is shown in FIG. 2. In such a case, a probe DNA is placed under the container convexes. In this case too, the distance between the probe DNA-immobilized face and the container convexes is preferably smaller than the minimum width of the fine particles. Another typical example thereof is the case where both the carrier and the container have an convex-concave structure.

It is possible to obtain the following effects and consequently to increase the intensity of the fluorescence after hybridization more than that in conventional methods, by stirring a target DNA-containing analyte solution with fine particles while using the carrier having a convex-concave area or the container having a convex-concave area.

When hybridization is performed in combination of a common flat plate-shaped DNA chip and a cover glass placed thereon, the distance between the cover glass and the DNA chip is approximately 10 μm at most. Use of fine particles larger in diameter results in clogging between the DNA chip and the cover glass, causing problems such as prohibition of movement of the fine particles and decrease in the advantageous effects of mixing fine particles. On the other hand, use of finer particles having a diameter of several μm, which is resistant to clogging between the cover glass and the DNA chip, for prevention of clogging and for movement of the fine particles by acceleration by gravity or vibration, only results in insufficient movement of the fine particles in the analyte solution, because the solution resistance becomes greater as the fine particles become smaller in size. Accordingly, there is still a problem that it is not possible to obtain favorable stirring effect with fine particles. Alternatively, expansion of the distance between the cover glass and the carrier for example with an O-ring and use of larger fine particles for sufficiently stirring cause the problem that the fluorescence intensity after hybridization deteriorates, presumably because the chip surface is damaged by the fine particles and the probe on the probe-immobilized surface is separated by collision of the fine particles.

As in the favorable embodiments of the present invention, it is possible to increase the size of fine particles at least up to the height of the concave area and convex in the convex-concave area, as shown in FIGS. 1 and 2, by using a carrier having a convex-concave area or a container having a convex-concave area. Thus, it is possible to obtain advantageous effects allowing sufficient stirring of the analyte solution with larger fine particles and preventing damage on the probe DNA-immobilized face, by stirring a target DNA-containing analyte solution with fine particles while using a carrier having a convex-concave area or a container having a convex-concave area.

In the method of stirring solution according to the present invention, the material for the container favorably used is not particularly limited. Examples of the materials for the container favorably used in the present invention include glass, plastics, and the like. When the shape of the container is flat plate, a glass plate such as cover glass or slide glass is favorably used, and when the container has convex-concave shape, a plastic material such as polymethyl methacrylate or polycarbonate, which is injection moldable, is preferable from a point of productivity.

The material for the carrier for use in the present invention is not particularly limited. Favorable materials for the carrier include glass and various polymers (polystyrene, polymethyl methacrylate, and polycarbonate).

When the carrier material is glass, for immobilization of a selective binding substance, the carrier may be treated with a silane coupling agent for generation of functional groups on the surface and the selective binding substance such as DNA may be immobilized on the carrier by using the functional groups. It is possible to form amino groups on the surface of glass by using, for example, an aminoalkylsilane, and to immobilize, for example, DNA thereon by the electrostatic force between the plus charge of the amino group and the minus charge of DNA.

In the present invention, use of a solid material containing a polymer having a structural unit represented by the following General Formula (1) particularly as the carrier surface for immobilization of a selective binding substance is advantageous, because the signal after hybridization becomes greater.

[Formula 1]

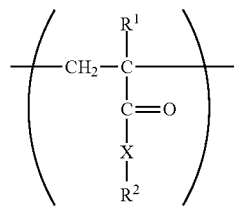

$X = O, NR^3, CH_2$

In General Formula (1), $R^1$, $R^2$, and $R^3$ each represent an alkyl or aryl group or a hydrogen atom. The polymer having a structural unit represented by the following General Formula (1) used is a homopolymer or a copolymer. At least one type of monomer is used as the raw material for the polymer, and the monomer is present as a double bond for polymerization or a functional group for polycondensation, ketone or carboxylic acid or the derivative thereof. The polymer more preferably has the structure represented by General Formula (1).

When the polymer having a structural unit represented by the following General Formula (1) is a copolymer, the polymer preferably contains the structural unit represented by the following General Formula (1) in an amount of 10% or more with respect to the total amount of all monomers. When the content of the structural unit represented by General Formula (1) is 10% or more, it is possible to form more carboxyl groups on the surface and immobilize more probe nucleic acids in the steps described below, leading to improvement in the S/N ratio.

The polymer in the present invention is a compound having a number-averaged polymerization degree of 50 or more. The number-averaged polymerization degree of the polymer is preferably in the range of 100 to 10,000, particularly preferably 200 or more and 5,000 or less. The number-averaged polymerization degree can be determined easily by measuring the molecular weight of a polymer according to a common method by GPC (gel permeation chromatography).

In General Formula (1), $R^1$ and $R^2$ each represent an alkyl or aryl group or a hydrogen atom, and may be the same as or different from each other. The alkyl group may be a straight-chain or branched group, and preferably has a carbon number of 1 to 20. The aryl group preferably has 6 to 18 carbon atoms, more preferably 6 to 12 carbon atoms. The functional group X is selected arbitrarily from O, $NR_3$, and $CH_2$. $R^3$ is a functional group defined similarly to $R^1$ and $R^2$.

In the present invention, the polymer on the carrier surface for immobilization of a selective binding substance is preferably a polymer having a functional group. Favorable examples of the polymers having a functional group include polyalkyl methacrylates (PAMA) such as polymethyl methacrylate (PMMA), polyethyl methacrylate (PEMA) and polypropyl methacrylate, and the like. Among them, particularly preferable is polymethyl methacrylate. Alternatively, polyvinyl acetate, polycyclohexyl methacrylate or polyphenyl methacrylate, or the like may also be used. Yet alternatively, a copolymer in combination of the polymer components above or a copolymer in combination of the polymer components and one or more other polymer components may also be used. The other polymers include polystyrene.

When the polymer is a copolymer, the rate of a carbonyl group-containing monomer, for example alkyl methacrylate, is preferably 10 mol % or more in all components. It is because it is possible in this way to form a greater number of carboxyl groups on the surface, to immobilize a greater amount of a probe nucleic acid, and consequently to improve the S/N ratio. The ratio of the monomer in the polymer structural units is more preferably 50 mole % or more.

For immobilization of a selective binding substance on a carrier containing a polymer having at least one structural unit represented by the following General Formula (1), it is preferable to pre-treat the carrier, forming carboxyl group on the carrier surface. The methods of forming carboxyl groups on the carrier surface include alkali or acid treatment, ultrasonication in hot water, exposure of the carrier to oxygen plasma, argon plasma, or radiation ray, and the like; but immersion of the carrier in alkali or acid for generation of surface carboxyl groups is preferable from the points of smaller damage on carrier and productivity. More specifically, the support may be immersed in an aqueous sodium hydroxide or sulfuric acid solution (preferable concentration: 1 to 20N) preferably at a temperature of 30° C. to 80° C. for 1 to 100 hours.

A thermoplastic copolymer containing an acid anhydride unit may be used as the polymer. The thermoplastic copolymer preferably has an acid anhydride unit (i). The acid anhydride unit (i) is a unit present on the skeletons of the main and side chains or at the terminals of a thermoplastic copolymer (A). The structure of the acid anhydride unit (i) is not particularly limited, and examples thereof include (meth)acrylic anhydride unit, glutaric anhydride unit, maleic anhydride unit, itaconic anhydride unit, citraconic anhydride unit, aconitic anhydride unit and the like; maleic and glutaric anhydride units are preferable; and among them, a glutaric anhydride unit represented by the following General Formula (2) is particularly preferable.

{Formula 2}

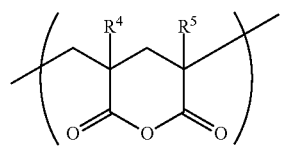

(2)

(in the Formula, $R^4$ and $R^5$ each independently represent a hydrogen atom or an alkyl group having 1 to 5 carbon atoms).

The structure of the thermoplastic copolymer is not particularly limited, if it has an acid anhydride unit (i), but the copolymer preferably contains an unsaturated carboxylic acid group (ii) represented by the following General Formula (3).

[Formula 3]

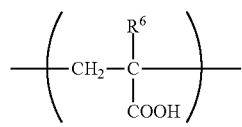

(3)

(wherein, $R^6$ represents a hydrogen atom or an alkyl group having 1 to 5 carbon atoms) The unsaturated carboxylic acid unit (ii) is an unit obtained by copolymerization of an unsaturated carboxylic acid monomer, and the unsaturated carboxylic acid monomer used then is not particularly limited, and any unsaturated carboxylic acid monomer copolymerizable with other vinyl compound may be used. Favorable unsaturated carboxylic acid monomers include the compounds represented by the following General Formula (4):

[Formula 4]

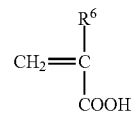

(4)

(wherein, $R^6$ represents a hydrogen atom or an alkyl group having 1 to 5 carbon atoms), maleic acid, and the hydrolysate of maleic anhydride, and the like; acrylic acid and methacrylic acid are preferable, and methacrylic acid is more preferable, from the point of heat stability. These monomers may be used alone or in combination of two or more. The thermoplastic copolymer (A) is not particularly limited, if it contains an acid anhydride unit (i), but preferably contains an unsaturated alkylcarboxylate esher unit (iii) represented by the following General Formula (5):

[Formula 5]

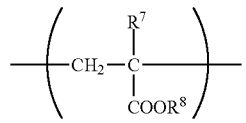

(5)

(wherein, $R^7$ represents a hydrogen atom or an alkyl group having 1 to 5 carbon atoms; $R^8$ represents an aliphatic or alicyclic hydrocarbon group having 1 to 6 carbon atoms or an aliphatic or alicyclic hydrocarbon group having 1 to 6 carbon atoms substituted with at least one hydroxyl group or halogen atom).

The unsaturated alkylcarboxylate ester unit (iii) is an unit obtained by copolymerization of an unsaturated alkylcarboxylate ester monomer, and the unsaturated alkyl carboxylate ester monomer is not particularly limited, and examples thereof include the following compounds represented by General Formula (6):

[Formula 6]

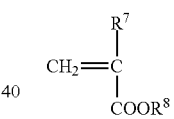

(6)

Presence of the carboxyl groups and the acid anhydrides on the carrier surface enables immobilization of a selective binding substance having an amino group or a hydroxyl group on the carrier surface by covalent bonding. When there are carboxyl groups on the carrier surface, various condensing agents such as dicyclohexylcarbodiimide and N-ethyl-5-phenylisoxazolium-3'-sulfonate are used for acceleration of the reaction of these groups. Among them, 1-ethyl-3-(3-dimethylaminopropyl) carbodiimide (EDC), which is less toxic and easily removed from the reaction system, is one of the condensation agents most effective for the condensation reaction of a selective binding substance with the carboxyl groups on the support surface. The condensation agent, for example EDC, may be used as it is mixed into a solution of the selective binding substance, or alternatively, a support carrying carboxyl groups previously formed on the surface is immersed in a solution of EDC and thus the surface carboxyl groups are activated. Use of the condensing agent, which is used as mixed with a solution of a selective binding substance, is advantageous, because it is effective in increasing the reaction yield and immobilizing a greater amount of the selective binding substance on carrier.

When the carboxyl groups on support surface are reacted with the amino group of a selective binding substance by using such a condensation agent, the selective binding substance is immobilized on the support surface by amide bond, while when the carboxyl groups on the support surface are reacted with the hydroxyl group of a selective binding substance, the selective binding substance is immobilized on the support surface by ester bond. The temperature when a sample containing a selective binding substance is allowed to react with the carrier is preferably 0 to 95° C. and more preferably 15° C. to 65° C. The processing period is normally 5 minutes to 24 hours and preferably 1 hour or more.

On the other hand, if the polymer has acid anhydride groups on the surface, the acid anhydride groups react with, for example, the amino group of the selective binding substance, forming covalent bonds, with or without such a condensing agent added.

Thus by immobilizing a selective binding substance preferably on the polymer surface it is possible to reduce non-specific adsorption of analyte, immobilize the selective binding substance covalently, tightly and at high density, and obtain a carrier higher in the hybridization efficiency with the analyte, presumably because the spatial degree of freedom of the immobilized selective binding substance is higher than that of the substance immobilized on glass.

When the carrier is prepared with a polymer containing a structural unit represented by General Formula (1) or (2), it is possible to produce fine concave-convex structured carrier more simply in a greater amount, for example by injection molding or hot embossing, than when the carrier is prepared with glass, ceramic, metal, or the like. In particular, injection molding, which allows easier mass production, is used favorably.

By immobilizing a selective binding substance on the polymer surface of the carrier favorably used in the present invention according to the method described above, it is possible to immobilize a selective binding substance covalently, tightly and at high density while reducing non-specific adsorption of the analyte. It is possible to obtain a carrier higher in hybridization efficiency with the analyte, presumably because the spatial degree of freedom of the immobilized selective binding substance is higher than that formed on glass.

The support carrying an immobilized selective binding substance thus obtained may be treated additionally after immobilization of the selective binding substance. It is possible, for example, to modify the immobilized selective binding substance by treatment such as heat treatment, alkali treatment, or surfactant treatment.

It is common that by using the selective binding substance-immobilized carrier, a fluorescent-labeled analyte and a carrier-immobilized selective binding substance are allowed to react in hybridization reaction, and the fluorescence from the product is determined in a device called scanner. The scanner deflects an excitation laser beam with an object lens and focuses the laser beam. However, when there is autofluorescence of the surface of the support, the fluorescence may cause noise and lead to deterioration in detection accuracy. For prevention thereof and also for prevention of the autofluorescence of the carrier itself, it is preferably to make the surface of the polymer having a structural unit represented by General Formula (1) or (2) appear black in color, by adding a black substance that does not emit light by laser irradiation. It is possible to reduce the autofluorescence of the carrier during detection, by using such a black carrier. The black carrier gives a favorable selective binding substance-immobilized carrier lower in noise and thus higher in S/N ratio.

The blackened support means a support of which the blackened area has a uniformly low spectroscopic reflectance not in a particular spectral pattern (e.g., without any particular peaks) and a uniformly low spectroscopic transmissibility not in a particular spectral pattern in the visible light range (wavelength: 400 to 800 nm).

In the present invention, the carrier has preferably a spectroscopic reflectance of 7% or less in the wavelength range of visible light (wavelength: 400 nm to 860 nm) and preferably a spectroscopic transmissibility of 2% or less in the same wavelength range. The spectroscopic reflectance is a spectroscopic reflectance including the regular reflected light from the support, as determined in an optical illuminator-detector system compatible with the condition C of JIS Z8722.

In the present invention, the support may be blackened by adding a black substance to the support, and favorable examples of the black substances include carbon black, graphite, titanium black, aniline black, oxides of metals such as Ru, Mn, Ni, Cr, Fe, Co and Cu, carbides of metals such as Si, Ti, Ta, Zr and Cr, and the like. Among the black substances, carbon black, graphite, titanium black are preferably contained; and carbon black is used particularly preferably, because it is easily dispersed uniformly in polymer.

These black substances may be contained alone or in combination of two or more.

Figure 6:
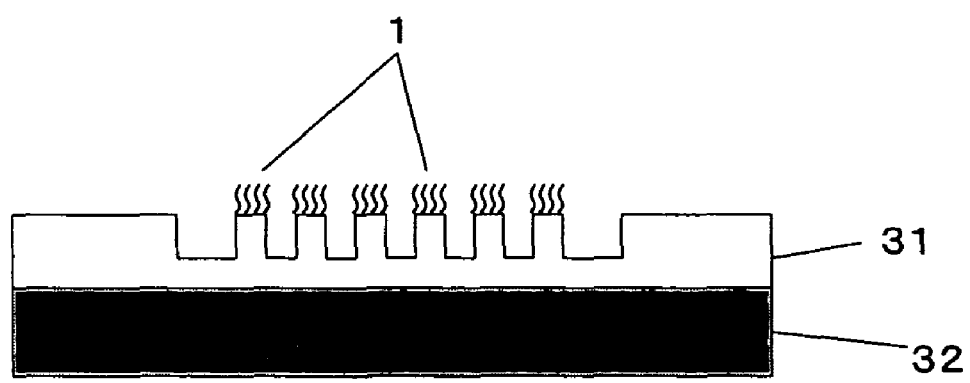
FIG. 6 is a conception diagram of a carrier having a support layer and a selective binding substance-immobilized layer.

As for the shape of the carrier in the present invention, a selective binding substance-immobilized layer of a polymer having at least one structural unit represented by the following General Formula (1) formed on a support layer resistant to heat deformation such as of glass or metal is preferable, because it is effective in preventing deformation of the carrier by heat or external force. An example of such structure is shown in FIG. 6. Polypropylene, glass, or a metal such as iron, chromium, nickel, titanium, or stainless steel is preferable for the support layer. In addition, the surface of the support layer is preferably finished in a plasma treatment with argon, oxygen, or nitrogen gas or treated with a silane-coupling agent, for improvement in adhesion between the support layer and the layer carrying an immobilized selective binding substance. Examples of the silane-coupling agents include 3-aminopropyltriethoxysilane, 3-aminopropyltrimethoxysilane, 3-aminopropyldiethoxymethylsilane, 3-(2-aminoethylaminopropyl) trimethoxysilane, 3-(2-aminoethylaminopropyl) dimethoxymethylsilane, 3-mercaptopropyltrimethoxysilane, dimethoxy-3-mercaptopropylmethylsilane, and the like.

A layer carrying an immobilized selective binding substance is formed on the support layer by any one of known means, for example, by spin coating with or dipping in a solution of a polymer dissolved in an organic solvent. More conveniently, the layer carrying an immobilized selective binding substance may be adhered to the support with an adhesive.

In the present invention, the "selective binding substance" means a substance that can selectively bind to an analyte substance directly or indirectly, and typical Examples thereof include nucleic acids, proteins, saccharides, and other antigenic compounds.

Particularly preferable as the "selective binding substances" is a nucleic acid. The nucleic acid may be DNA, RNA, or PNA. Single strand nucleic acids having a particular base sequence selectively hybridizes with and binds to a single strand nucleic acid having the base sequence complementary to the base sequence or the part thereof, and thus are included in the "selective binding substances" according to the present invention.

Examples of the proteins include antibodies, antigen-binding antibody fragments such as Fab fragments and F (ab') 2 fragments, and various antigens. Antibodies and their antigen-binding fragments that selectively bind to respective complementary antigens and antigens that selectively bind to respective complementary antibodies are also included in "selective binding substances". Polysaccharides are preferably as the saccharides, and examples thereof include various antigens.

Alternatively, an antigenic substance other than protein or saccharide may be immobilized.

The selective binding substance for use in the present invention may be a commercially available product or a substance prepared from living cell or the like.

The selective binding substance for use in the present invention is preferably a nucleic acid, and among nucleic acids, preferable are nucleic acids having a length of 10 to 100 bases called oligonucleic acids, which are easily prepared in synthesizer and allows modification of the amino group on the nucleic acid terminal for immobilization thereof on the carrier surface. Further, the length of the oligonucleic acid is preferably 20 to 100 bases, because the hybridization efficiency is lower with an oligonucleic acid having less than 20 bases, and particularly preferably in the range of 40 to 100 bases, for ensuring the stability of hybridization efficiency.

Examples of the analyte substances to be processed in the method of stirring a solution according to the present invention include, but are not limited to, nucleic acids to be evaluated, such as genes of pathogenic bacteria and viruses and causative genes of genetic diseases, or the partial region thereof; various antigenic biological components; antibodies to pathogenic bacteria and viruses; and the like.

In the method of stirring a solution according to the present invention, examples of the samples containing the analyte substances above include, but are not limited to, body fluids such as blood, serum, blood plasma, urine, feces, spinal fluid, saliva, and various tissue fluids and various foods and drinks or diluents thereof, and the like.

In addition, the analyte nucleic acid may be prepared by labeling a nucleic acid extracted from blood or cell according to a common method or by amplifying the nucleic acid by a nucleic acid-amplifying method such as PCR by using it as a template. It is possible to improve measurement sensitivity drastically, when an analyte prepared by a nucleic acid-amplifying method such as PCR using a nucleic acid as a template is used. When an amplified nucleic acid product is used as the analyte substance, it is possible to label the amplified nucleic acid by performing amplification in the presence of a nucleotide-3-phosphate labeled with a fluorescent material or the like. When the analyte substance is an antigen or antibody, the analyte substance, antigen or antibody, may be directly labeled by a common method, or alternatively, the analyte substance, antigen or antibody, may be first bound to a selective binding substance; after washing of the support, the antigen or antibody is allowed react with a labeled antibody or antigen that reacts in the antigen-antibody reaction; and then, the labels bound to the support is analyzed.

Preferably in the method of stirring a solution according to the present invention, a selective binding substance is allowed to react with an analyte substance.

The step of allowing an immobilized substance to react with an analyte substance in the method of stirring a solution according to the present invention may be performed entirely, similarly to that in conventional methods. The reaction temperature and period may be selected arbitrarily, for example, according to the chain length of the nucleic acid to be hybridized and the kinds of the antigen and/or the antibody involved in the immune reaction, but the reaction is generally carried out at approximately 35° C. to 70° C. approximately for 1 minute to more than ten hours in the case of nucleic acid hybridization, and generally, at room temperature to approximately 40° C. for approximately 1 minute to several hours in the case of immune reaction.

The method of stirring a solution according to the present invention was found to have the following advantages, in addition to the improvement in intensity of the signal after hybridization. Conventional methods of DNA-chip hybridization caused a problem of difficulty in data analysis, because the fluorescence intensity after hybridization is lower and distribution of fluorescence intensity on the spot where a probe DNA was immobilized is donut-shaped. However, the method of stirring a solution according to the present invention has an advantage that it improves the fluorescence intensity drastically and prevents the donut-shaped distribution of the fluorescence intensity on the spot.

EXAMPLES

The present invention will be described in more detail with reference to the following Examples. It should be understood that the present invention is not restricted by the following Examples.

Example 1

Preparation of DNA-Immobilized Support

A mold for injection molding was prepared according to a known LIGA (Lithographie Galvanoformung Abformung) process, and a PMMA substrate having the shape described below was prepared by injection molding. The PMMA used in this Example had an average molecular weight of 50,000 and contained carbon black (#3050B, manufactured by Mitsubishi Chemical Corp.) at a ratio of 1 wt %, and the substrate was black in appearance. When the spectroscopic reflectance and transmissibility of the black substrate were determined, the spectroscopic reflectance was 5% or less at a wavelength in the visible light range (wavelength: 400 to 800 nm), and the transmissibility was 0.5% or less at a wavelength in the same range. The substrate had a uniformly flat spectrum without a particular spectral pattern (e.g., peaks) both in spectroscopic reflectance and transmissibility in the visible light range. The spectroscopic reflectance is a spectroscopic reflectance including regular reflectance from the support, as determined by using a device equipped with an optical illuminator-detector system (CM-2002, manufactured by Minolta Camera) compatible with the condition C of JIS Z 8722.

The shape of support was 76 mm in length, 26 mm in width, and 1 mm in thickness, and the surface was flat except in the central area of the substrate. A recessed area of 10 mm in diameter and 0.2 mm in depth 0.2 mm is formed on the center of the carrier, and 64 (8×8) convexes having a top face diameter of 0.2 mm and a height of 0.2 mm were formed in the recess. The difference between the height of convex top face (average of the heights of 64 convexes) in the convex-concave part and the height of the flat area was 3 μm or less, when determined. In addition, the variation in height of the 64 convex top faces (difference in height between the highest and the lowest convex top faces), and the difference between the height of convex top face in the convex-concave surfaced area and the height of the flat area, when determined, were both 3 μm or less. Further, the pitch of the convexes in the convex-concave surfaced area (distance between a convex center to another convex center next to it) was 0.6 mm.

The PMMA carrier was immersed in aqueous 10 N sodium hydroxide solution at 65° C. for 12 hours. The carrier was washed with purified water, aqueous 0.1 N HCl solution, and purified water in that order, forming carboxyl groups on the carrier surface.

(Immobilization of Probe DNA)

A DNA having the sequence shown by SEQ ID NO: 1 (60 base, 5' terminal aminated) was prepared. The DNA having the sequence of SEQ ID NO: 1 has an aminated 5'-terminal.

The DNA was dissolved in purified water to a concentration of 0.3 nmol/μl, to give a stock solution. For spotting on the carrier, prepared was a solution of the probe diluted with PBS (a solution of 8 g of NaCl, 2.9 g of $Na_2HPO_4$-$12H_2O$, 0.2 g of KCl, and 0.2 g of $KH_2PO_4$ dissolved in 1 L of purified water containing hydrochloric acid for pH adjustment, pH: 5.5) to a final concentration of 0.03 nmol/μl, containing additionally 1-ethyl-3-(3-dimethylaminopropyl)carbodiimide (EDC) at a final concentration of 50 mg/ml, for condensation of the carboxyl groups on the carrier surface with the terminal amino group of the probe DNA. The mixture solution was then spotted on the top face of the convexes of the carrier with a glass capillary. The carrier was then placed in a tightly sealed plastic container, incubated under the condition of 37° C. and a humidity of 100% for approximately 20 hours, and the washed with purified water.

Figure 7:
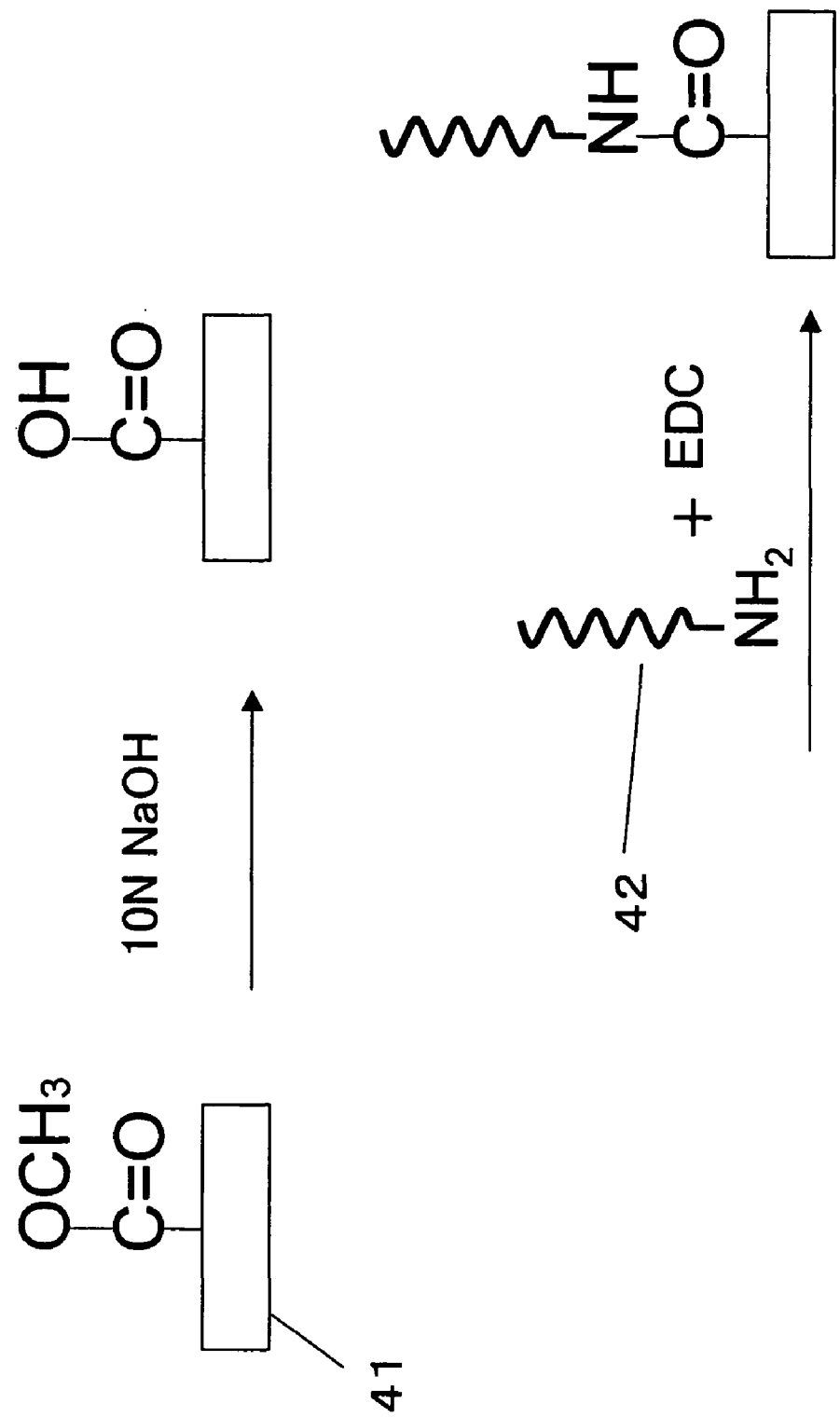
FIG. 7 is a reaction scheme when a selective binding substance is immobilized on a PMMA surface.

FIG. 7 shows the reaction scheme. (Preparation of sample DNA)

A DNA having a sequence of SEQ ID NO: 4 (968 bases), which hybridizes with the probe DNA immobilized on the DNA-immobilized carrier, was used as the analyte DNA. The preparative method is as follows:

DNA's of SEQ ID NOS 2-3 were prepared. These DNA's were respectively dissolved in purified water to a concentration of 100 μM. The DNA was amplified in PCR reaction (Polymerase Chain Reaction) by using a plasmid DNA (Takara Bio Inc., product number: 3100), (SEQ ID NO: 5: 2264 base) as the template and the DNAs having sequences of SEQ ID NOS 2-3 as the primers.

The PCR condition is as follows: ExTaq (2 μl), 10×Ex-Bufer (40 μl) and dNTp Mix (32 μl) (these reagents were attached to the Product Number RR001A manufactured by Takara Bio Inc.), a solution of SEQ ID NO: 2 (2 μl) and a solution of SEQ ID NO: 3 (2 μl) and solution of template (SEQ ID NO: 5) (0.2 μl) were mixed and diluted with purified water to a total volume of 400 μl. The liquid mixture was divided into four micro tubes, and the PCR reaction was performed by using a thermal cycler. The product was purified by ethanol precipitation and dissolved in 40 μl of purified water. Electrophoretic analysis of part of the solution after PCR reaction confirmed that the base length of the amplified DNA was approximately 960 bases and the DNA of SEQ ID NO: 4 (968 bases) was amplified.

Then, a 9-base random primer (manufactured by Takara Bio Inc., product number: 3802) was dissolved to a concentration of 6 mg/ml, and 2 μl thereof is added to the DNA solution purified after the PCR reaction.

The solution was heated at 100° C. and quenched on ice. 5 μl of the buffer attached to Klenow Fragment (manufactured by Takara Bio Inc., Product Number 2140AK) and 2.5 μl of a dNTP mixture (containing dATP, dTTP, and dGTP each at a concentration of 2.5 mM and dCTP at a concentration of 400 μM) were added thereto. Further, 2 μl of Cy3-dCTP (manufactured by Amersham Pharmacia Biotech, Product Number PA53021) was added. After addition of 10 U of Klenow Fragment to the solution, the mixture was incubated at 37° C. for 20 hours, to give a Cy3-labeled sample DNA. Use of the random primer during labeling resulted in fluctuation in the length of the sample DNA. The longest sample DNA is the DNA of SEQ ID NO: 4 (968 bases). Electrophoretic analysis of part of the sample DNA solution showed the most intensive band in the area approximately corresponding to 960 bases and bands slightly smeared in the area corresponding to shorter base lengths. The product was then purified by ethanol precipitation and dried.

The labeled analyte DNA was dissolved in 400 μl of a solution containing 1 wt % BSA (bovine serum albumin), 5×SSC (5×SSC is a solution 20×SSC (manufactured by sigma) diluted four times with purified water, 10×SSC is a solution of 20×SSC diluted twice with purified water, 20×SSC diluted twice is 10×SSC, that diluted 100 times is 0.2×SSC), 0.1 wt % SDS (sodium dodecylsulfate), and 0.01 wt % salmon sperm DNA solution (concentrations above; final concentrations), to give a stock solution for hybridization.

In the following Examples and Comparative Examples, the stock solution above diluted 200 times with 1 wt % BSA, 5×SSC, 0.01 wt % salmon sperm DNA, and 0.1 wt % SDS solution (all, final concentrations) was used as the analyte solution during hybridization, unless specified otherwise. The concentration of the analyte DNA in the solution was determined to be 1.5 ng/μl.

(Surface-Modification of Glass Beads)

10 g of glass beads having a diameter of 150 μm were immersed in 10 N NaOH solution and then, washed with purified water. Then, APS (3-aminopropyltriethoxysilane; manufactured by Shin-Etsu Chemical Co., Ltd.) was dissolved in water to a concentration of 2 wt %, and the glass beads were immersed therein for 1 hour, and, after removal, dried at 110° C. for 10 minutes. In this way, amino groups were introduced on the surface of the glass beads.

Then, 5.5 g of succinic anhydride was dissolved in 335 ml of 1-methyl-2-pyrrolidone. 50 ml of 1 M sodium borate (containing 3.09 g of boric acid and sodium hydroxide for pH adjustment in 50 ml of purified water, pH: 8.0) was added to the succinic acid solution. The glass plate above was immersed in the liquid mixture for 20 minutes. After immersion, the glass plate was washed with purified water and dried. In this manner, amino groups on the glass plate surface and succinic anhydride were allowed to react with each other, introducing carboxyl groups on the glass surface.

(Hybridization)

The analyte DNA was applied on the probe DNA-immobilized carrier obtained above, for hybridization. Specifically, 50 μl of the solution for hybridization was applied dropwise onto the carrier carrying the probe nucleic acid immobilized on the convexes prepared above; 2 mg of the surface-modified glass beads were added to the concave area of the carrier; and the support was covered with a cover glass. In addition, the cover glass was sealed with a paper bond, for preventing vaporization of the hybridization solution. A cover glass carrying photoresists having a thickness of 8 μm and a width of 1 mm formed by photolithography on two opposing sides among four sides was used. In this way, the distance (gap) between the carrier convex and the cover glass was kept 8 μm during hybridization. It was fixed in a plastic container on the revolving plate of a microtube rotator (manufactured by As One, product number: 1-4096-01), and incubated under the condition of 65° C. and a humidity of 100% for 10 hours. The rotational frequency of the rotator then was 3 rpm, and the angle was in the direction perpendicular to the revolving plate of the rotator. In addition, the probe DNA-immobilized face of the carrier was placed in the direction perpendicular to the revolving plate of the rotator. After incubation, the cover glass was removed from the carrier, and the carrier was washed and dried.

(Measurement)

The carrier after treatment was placed in a scanner for DNA chip (GenePix4000B, manufactured by Axon Instruments), and the fluorescence intensity therefrom was determined under the conditions of a laser output of 33% and a photomultiplier gain of 500. The results are summarized in Table 1. The fluorescence intensity is an average of the fluorescence intensity in the spot.

Although glass beads were used in the present Example, results similar to those in Table 1 were obtained when ceramic beads or Teflon (registered trademark) beads were used.

Comparative Example 1

An experiment was performed without added glass beads. The experiment procedure was similar to that in Example 1, except that no glass bead was mixed during hybridization. Results are summarized in Table 1.

It was found that the fluorescence intensity was lower than that in Example 1. In addition, the fluorescence intensity distribution on carrier convexes was uneven (donut-shaped) in Comparative Example 1, but the fluorescence intensity distribution on carrier convexes was almost uniform in Example 1.

Comparative Example 2

An experiment was performed with a flat PMMA carrier having no convex-concave area. The experiment procedure was similar to that in Example 1, except that (1) a flat carrier was used, (2) a probe DNA was spotted in a special-purpose machine (Gene Stamp II, manufactured by Nippon Laser & Electronics Co., Ltd.), and (3) an opening for bead stirring between the carrier and the cover glass was formed by bonding a polyester film having a thickness of 200 μm and a width of 1 mm on four sides of the cover glass and beads and an analyte solution were mixed in the opening for hybridization. Comparison with the results in Example 1 reveals that the fluorescence intensity is lower. Results are summarized in Table 1. It was also confirmed that there was damage on the spot that was not found in Example 1. It seemed that the beads were the cause of the damage on the probe-immobilized face during hybridization.

When the experiment was repeated in another Comparative Example after the diameter of the beads was changed to 1 μm, the fluorescence intensity was further lower at approximately 1,500. Apparently, it is because of the phenomenon that the beads were less mobile by resistance of the hybridization solution.

Example 2

An experiment on stirring efficiency was performed by using air bubbles. The experiment procedure was similar to that in Example 1, except that 0.9 μL of air bubble was injected with a microsyringe, instead of adding glass beads, when a cover glass is placed in the hybridization step. The carrier was fixed in such a direction that the revolving plate of rotator tilted into the vertical direction and the probe-immobilized face of the carrier became in parallel, and rotated, allowing air bubbles to migrate only around the sealed analyte solution. In this way, air bubbles were kept separated from the probe-immobilized face. Results are summarized in Table 1. Advantageous effects similar to those in Examples were observed.

Example 3

An experiment similar to Comparative Example 2 was performed, by using a container for solution 4 having the cross-sectional structure shown in FIG. 2 instead of a glass cover. That is, the convex-concave structure was formed not on the carrier but on the cover. The container and the flat PMMA carrier were placed carefully in the spatial relationship shown in FIG. 2. In subsequent hybridization while the beads are agitated, it was possible to move the glass beads without contact thereof with the probe DNA-immobilized face, because the distance between the probe DNA-immobilized face and the container for solution 4 was smaller than the diameter of the glass beads 2. Results are summarized in Table 1. The fluorescence intensity obtained was similar to that in Example 1. Considering the results in Comparative Example 2 as well, it seems important that the beads do not become in contact with the probe-immobilized face. In the method of the present Example, accurate positioning of the cover convexes and the probe-immobilized region is important.

Comparative Example 3

An experiment was performed without stirring with beads by using a flat PMMA carrier having no concave-convex area. The experiment was done by operation and measurement in a similar manner to Comparative Example 2, except that no bead was added to the hybridization solution and there was no rotation. Results are summarized in Table 1.

TABLE 1

|  | Example 1 | Example 2 | Example 3 | Comparative Example 1 | Comparative Example 2 | Comparative Example 3 |
|---|---|---|---|---|---|---|
| Target concentration (ng/μL) | 1.5 | 1.5 | 1.5 | 1.5 | 1.5 | 1.5 |
| Substrate shape | convex-concave | convex-concave | Flat plate | convex-concave | Flat plate | Flat plate |
| Gap (μm) | 8 | 8 | 8 | 8 | 200 | 8 |
| Stirring method | Bead | Air bubble | Bead | No | Bead | No |
| Rotation | Yes | Yes | Yes | Yes | Yes | No |
| Fluorescence intensity | 12000 | 8800 | 11800 | 2900 | 3900 | 700 |
| Noise | 45 | 50 | 300 | 50 | 300 | 300 |

Example 4

Five kinds of glass beads in Example 1 were used in the experiment. The experiment procedure was similar to that in Example 1, and the diameter of the glass beads used was 10, 20, 50, 100, or 200 μm. Results are summarized in Table 2.

Comparative Example 4

An experiment was performed in a similar manner to Example 1, except that the diameter of the glass beads was changed to 300 µm or 400 µm. The results are summarized in Table 2.

TABLE 2

|  | Example 4 | | | | | Comparative Example 4 | |
|---|---|---|---|---|---|---|---|
| Size (µm) | 10 | 20 | 50 | 100 | 200 | 300 | 400 |
| Fluorescence intensity | 8200 | 10500 | 12700 | 12000 | 12500 | 3100 | 3000 |

As apparent from the table, beads of 10 to 200 µm in diameter were distinctively higher in stirring efficiency, but the beads of Comparative Example 4 of 300 or 400 µm in diameter were not distinctively effective. Because the distance between the carrier concave and the cover glass was 208 µm, it seems that the beads of 300 or 400 µm forcibly added could not migrate as they are held in the opening between the cover glass and the carrier. The results in Examples and Comparative Examples reveal that difficulty in bead movement leads to decrease in fluorescence intensity. In addition, the results in Example 4 indicates that the bead size is preferable 10 µm or more and more preferably 20 µm or more.

Example 5

An experiment was performed in a similar manner to Example 1 by using a carrier in the shape having the following characteristics. A recessed area of 10 mm in diameter and 0.3 mm in depth is formed on the center of the substrate, and 64 (8×8) convexes having a top face diameter of 0.2 mm and a height of 0.3 mm were formed in the recess. Other characteristics of the carrier and the experimental procedure were similar to those in Example 1. The diameter of the glass beads used was 10, 20, 50, 100, 200, or 300 µM. Results are summarized in Table 3.

Comparative Example 5

An experiment was performed in a similar manner to Example 5, except that the diameter of the glass beads used was 400 µm. The results are summarized in Table 3.

TABLE 3

|  | Example 5 | | | | | | Comparative Example 5 |
|---|---|---|---|---|---|---|---|
| Size (µm) | 10 | 20 | 50 | 100 | 200 | 300 | 400 |
| Fluorescence intensity | 8800 | 11000 | 13000 | 12000 | 12700 | 12000 | 2700 |

Beads of 10 to 300 µm in diameter were distinctively higher in stirring efficiency, but the beads of 400 µm in diameter were not distinctively effective. Because the distance between the carrier concave and the cover glass was 308 µm, it seems that the beads of 400 µm forcibly added could not migrate as they are held between the cover glass and the carrier. The result in Examples and Comparative Examples reveals that difficulty in bead movement leads to decrease in fluorescence intensity. In addition, the results in Example 5 indicates that the bead size is preferable 10 µm or more and more preferably 20 µm or more.

Example 6

An experiment was performed by using a carrier having convexes varying in height. The convexes on the injection-molded PMMA substrate used in Example 1 were polished with a polishing paper, to make variation in the height of the convex top faces. Specifically, a support (support A) having four convexes lower by 30 µm than other convexes (standard convex) and a support (support B) having four convexes lower by 50 µm than other convexes were prepared. The difference in height between the face of the convexes other than the lower convexes (standard convex) and the face of the flat area was 3 µm or less. A probe DNA for spotting was prepared in a similar manner to Example 1. Then, the probe DNA solution was spotted on the faces of four standard convex and four lower convexes in a similar manner to Example 1, and further, a hybridization analyte DNA was prepared and hybridized in a similar manner to Example 1. Hybridization and measurement were performed in a similar manner to Example 1. The average of the fluorescence intensities from the faces of standard convexes and the average of the fluorescence intensities from the faces of the lower convexes are summarized in Table 4.

TABLE 4

|  | Example 6 | | | |
|---|---|---|---|---|
|  | Carrier a | | Carrier b | |
|  | Standard convex area | Convex area lower by 30 µm | Standard convex area | Convex area lower by 30 µm |
| Fluorescence intensity | 13000 | 120000 | 12600 | 8900 |

The results show that a S/N ratio similar to that in Examples 1 and 2 could be obtained even on a substrate where there is some fluctuation in the height of convexes (50 µm or less).

Example 7

The case where there is some difference in height between the top face of the convexes and the flat area was also studied.

The convexes on the injection-molded PMMA substrate used in Example 1 were polished with a polishing paper, to make two supports respectively having differences in height by 30 µm (support C) and 50 µm (support D) between the faces of the flat area and the convex top face. Namely, the support C has convexes higher by 30 µm than the flat area. A probe DNA for spotting was prepared and spotted onto the face of the convexes; an analyte DNA was prepared; and glass beads are surface-modified in a similar manner to Example 1. Hybridization was performed in a similar manner to Example 1, except that a silicon sheet (thickness: 60 µm) was bonded instead of forming a polymer on the cover glass. The number of the convexes on the carrier on which the DNA solution was spotted was four. The average of the fluorescence intensities of the DNA-bound spots (4 areas) was determined.

The results are summarized in Table 5.

TABLE 5

|  | Example 7 | |
|---|---|---|
|  | Carrier c | Carrier d |
| Fluorescence intensity | 11500 | 8700 |

The results show that a S/N ratio equivalent to that in Example 1 could be obtained even where there is some difference in height between the flat area top face and the convex top face (50 μm or less).

Example 8

The substrate sealed with a cover glass and paper bond in Example 1 was placed in a Voltex shaker (manufactured by Scientific Industries, Inc.), and hybridization stirring was performed by movement of glass bead by vibration. The experiment procedure was similar to that in Example 1, except that the rotator was replaced with a Voltex shaker. Results are summarized in Table 6. High fluorescence intensity was observed.

Example 9

Figure 8:
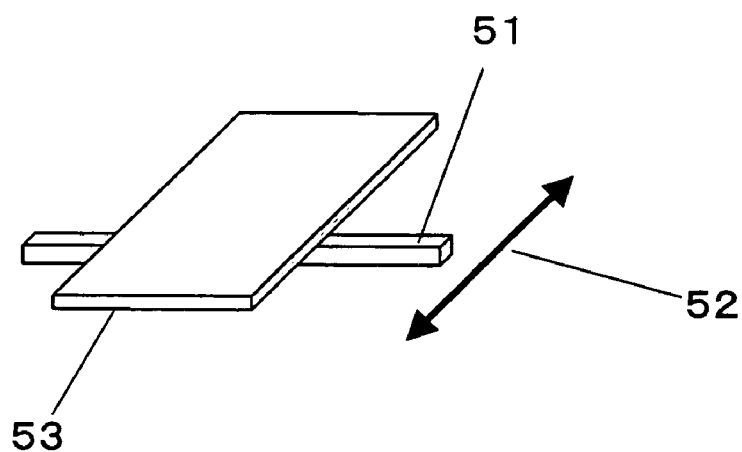
FIG. 8 is a schematic view of the jig used in Example 9.

In the experiment, the hybridization solution was stirred by adding magnetic beads during hybridization and moving the magnetic beads while changing the external magnetic field. A device shown in FIG. 8, in which a magnet moves reciprocally, was first prepared by the inventors. The experiment procedures, (preparation of DNA-immobilized carrier) (immobilization of probe DNA) (preparation of analyte DNA) and (measurement), were similar to those in Example 1. Hybridization was performed in a similar manner to Example 1, except that 1 mg of magnetic beads having a diameter of 50 μm (manufactured by Trial Corp.) were added into the carrier concave, replacing glass beads, and the rotator was replaced with the self-made machine described above. Results are summarized in Table 6. High fluorescence intensity was observed.

Comparative Example 6

An experiment was performed in a similar manner to Example 9 by using a flat PMMA carrier having no convex-concave area. The experiment procedure was similar to that in Example 1, except that (1) a flat carrier was used, (2) a probe DNA was spotted in a special-purpose machine (Gene Stamp II, manufactured by Nippon Laser & Electronics Co., Ltd.), (3) an opening for bead stirring between the carrier and the cover glass was formed by bonding a polyester film having a thickness of 200 μm and a width of 1 mm on four sides of the cover glass and magnetic beads and an analyte solution was mixed in the opening for hybridization, and (4) the carrier was placed in the self-made machine shown in FIG. 8 with the cover glass face facing downward. With the cover glass face placed downward, the magnetic beads, which are attracted onto the cover glass face, are expected to stir the solution without contact with the opposing probe-immobilized face. Results are summarized in Table 6. Only a fluorescence intensity lower than that in Example 9 was obtained. In addition, there was damage observed on the spot where there was none in Example 9. In Comparative Example 6 the magnetic beads were attracted by a magnet aggregated and solidified over the entire width of 200 μm of a polyester film; and the aggregate, which was forcibly migrated, became in contact with the probe-immobilized face.

TABLE 6

|  | Example 8 | Example 9 | Comparative Example 6 |
|---|---|---|---|
| Kind of bead | Glass | Magnetic material | Magnetic material |
| External force | Vibration | Magneitic force | Magneitic force |
| Fluorescence intensity | 9900 | 7800 | 2800 |

Example 10

An experiment was performed in a similar manner to Example 1, except that beads of yttria-stabilized zirconia (containing yttria in an amount of 2.5 mol % with respect to zirconia) having a diameter of 125 μm were used. As a result, the fluorescence intensity after hybridization was almost similar. However, the beads were less mobile even in movement of the solution when 2 mg of beads were mixed and a cover glass is placed thereon, and thus, it was easier to place the carrier. It is because the density of the zirconia beads is 6.05 g/cm$^3$ thrice higher than that of glass.

Example 11

Figure 9:
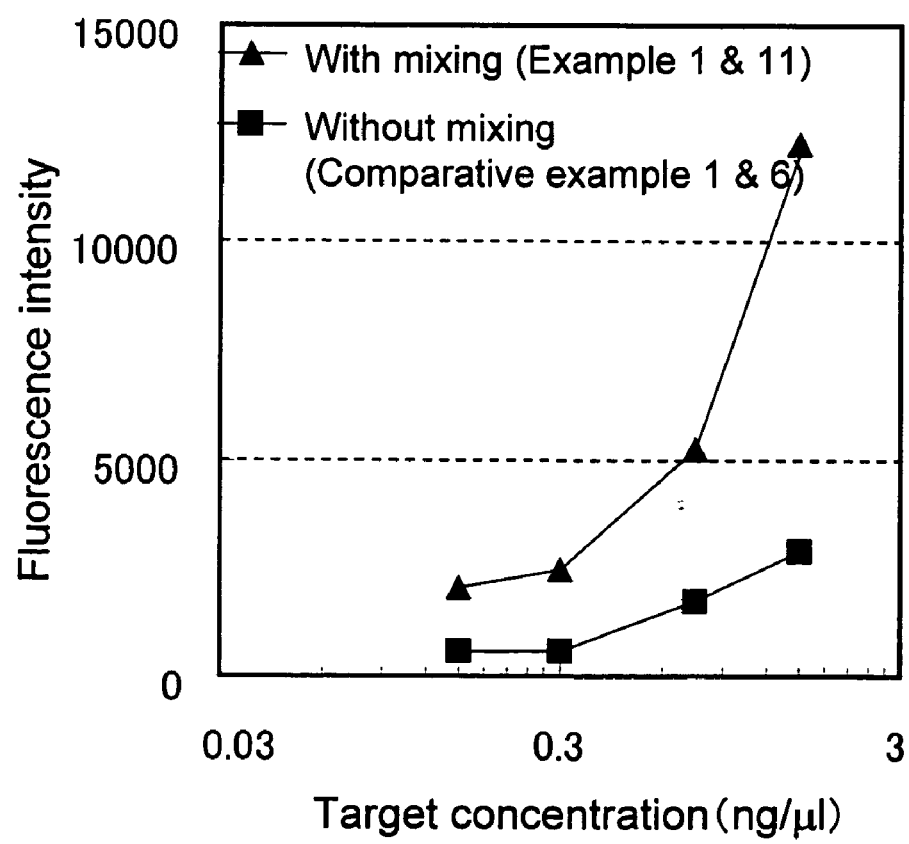
FIG. 9 shows the change in fluorescence intensity when the target concentration is altered.

An experiment was performed in a similar manner to Example 1, except that the concentration of the analyte DNA was adjusted to 0.73, 0.29, or 0.15 ng/μL. Results are summarized in FIG. 9. The results in Example 1 and Comparative Example 1 were also shown in FIG. 9.

Comparative Example 7

An experiment was performed in a similar manner to Example 1, except that the concentration of analyte DNA was adjusted to 0.73, 0.29, or 0.15 ng/μL. Results are summarized in FIG. 9. The results in Example 1 and Comparative Example 1 were also shown in FIG. 9.

It was thus possible to determine the stirring efficiency by using beads under four conditions different in analyte concentration.

Example 12

An experiment for detecting SNP (single nucleotide polymorphism) with a DNA chip was performed. The experiment procedures, (preparation of DNA-immobilized carrier), (preparation of analyte DNA), (surface-modification of glass beads) (hybridization) and (measurement), were similar to those in Example 1. The concentration of the analyte DNA was 1.5 ng/μl. However, hybridization was performed at 42° C. The probe DNA used was 5'-terminal-aminated DNAs having SEQ ID NOS 6 and 7 prepared. The DNA's having SEQ ID NOS 6 and 7 are different from each other only by one base. The 10-base T sequence was 5'-terminal of the two probes is not complimentary with the analyte DNA, while the other region in the DNA of SEQ ID NO: 6 (20 bases) is completely complimentary with the analyte DNA. The two kinds of DNA's were immobilized on the carrier convexes by a procedure similar to that in Example 1. Results are summarized in Table 7. It is possible to detect difference of only one base between two kinds of probe DNAs by the method according to the present invention.

TABLE 7

| | Example 12 | |
|---|---|---|
| SEQ ID NO | 6 | 7 |
| Fluorescence intensity | 10500 | 3200 |

INDUSTRIAL APPLICABILITY

The present invention provides a method of stirring a solution that accelerates the reaction of a carrier-immobilized selective binding substance with an analyte substance and detects a trace amount of analyte at high signal intensity and high S/N ratio. Thus, it is possible to improve the signal intensity and the S/N ratio (i.e., sensitivity) of a selective binding substance-immobilized carrier such as DNA chip, by using the stirring method according to the present invention, and thus, the method is allows analysis of a trace amount of clinical sample. The present invention enables diagnosis and examination in the clinical setting by using a selective binding substance-immobilized carrier such as DNA chip.

The invention claimed is:

1. A method of stirring a solution for contacting a selective binding substance immobilized on a surface of a carrier with a solution containing an analyte substance reactive with the selective binding substance, comprising the steps of:
adding fine particles into the solution,
sealing the fine particles in the solution with a seal and the carrier, and stirring the solution by moving the fine particles sealed in the solution by using the carrier and/or a container which have a convex-concave structure such that the fine particles do not contact the selective binding substance-immobilized surface, wherein
(i) the carrier has a convex-concave structure and the selective binding substance is immobilized on the top face of the convexes, and a minimum width of the fine particles is greater than a minimum distance between the selective binding substance-immobilized surface and the container, and/or
(ii) the container for the solution has a convex-concave structure, the selective binding substance is immobilized on the carrier under the container convexes, and a minimum width of the fine particles is greater than a minimum distance between the selective binding substance-immobilized surface and the container convexes.

2. A method of stirring a solution for contacting a selective binding substance immobilized on a top face of convexes of a carrier with a solution containing an analyte substance reactive with the selective binding substance, comprising the steps of:
adding fine particles into the solution containing the analyte substance,
sealing the fine particles in the solution with a seal and the carrier, and
moving the fine particles sealed in the solution, wherein the solution is in a container, and a minimum width of the fine particles is greater than a minimum distance between the selective binding substance-immobilized surface and the container.

3. The method according to claim 1 or 2, wherein the solution is stirred by movement of the fine particles, the carrier has a convex-concave surface, the selective binding substance is immobilized on the top face of the convexes of the carrier, and the fine particles move in a concave area.

4. The method according to claim 1 or 2, wherein the carrier has a flat area and a convex-concave area, the selective binding substance is immobilized on a top face of the convexes of the carrier, the height of the top face of the convexes is almost the same, and the difference in height between a flat area and the top face of the convexes is 50 µm or less.

5. The method according to claim 2, wherein the fine particles are forced to move by gravity, magnetic force, vibration of carrier, or a combination thereof.

6. The method according to claim 3, wherein a maximum width of the fine particles is 10 µm or more and less than the difference in height between the top face of convexes and the concave area.

7. The method according to claim 1 or 2, wherein the selective binding substance is a nucleic acid.

8. The method according to claim 1 or 2, wherein the selective binding substance reacts with the analyte substance.

9. The method according to claim 1, wherein the fine particles are forced to move by gravity, magnetic force vibration of carrier, or a combination thereof.

* * * * *

SEQUENCE LISTING

<160> NUMBER OF SEQ ID NOS: 7

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      plasmid pKF3 sequence

<400> SEQUENCE: 1
acattttgag gcatttcagt cagttgctca atgtacctat aaccagaccg ttcatctgga        60

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      plasmid pKF3 sequence

<400> SEQUENCE: 2
gggcgaagaa gttgtccata                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      plasmid pKF3 sequence

<400> SEQUENCE: 3
gcagagcgag gtatgtaggc                                                    20

<210> SEQ ID NO 4
<211> LENGTH: 968
<212> TYPE: DNA
<213> ORGANISM: Artificial Sequence
<220> FEATURE:
<223> OTHER INFORMATION: Description of Artificial Sequence: Synthetic
      plasmid pKF3 sequence

<400> SEQUENCE: 4
gggcgaagaa gttgtccata ttagccacgt ttaaatcaaa actggtgaaa ctcacccagg        60
gattggctga gacgaaaaac atattctcaa taaacccttt agggaaatag gccaggtttt       120
caccgtaaca cgccacatct tgcgaatata tgtgtagaaa ctgccggaaa tcgtcgtggt       180
attcactcca gagcgatgaa aacgtttcag tttgctcatg gaaaacggtg taacaagggt       240
gaacactatc ccatatcacc agctcaccgt ctttcattgc catacgaaat tccgtatgag       300

-continued

```
cattcatcag gcgggcaaga atgtgaataa aggccggata aaacttgtgc ttattttcct      360
ttacggtctt taaaaaggcc gtaatatcca gatgaacggt ctggttatag gtacattgag      420
caactgactg aaatgcctca aaatgttctt tacgatgcca ttgggatata tcaacggtgg      480
tatatccagt gattttttc tccatttag cttcctagc tcctgaaaat ctcgataact         540 caaaaatac gcccggtagt gatcttattt cattatggtg aaagttggaa cctcttacgt      600
gccgatcaac gtctcatttt cgccaaaagt tgcccaggg cttcccggta tcaacggga      660 caccaggatt tatttattct gcgaagtgat cttccgttcg acggagttcc actgagcgtc    720
agaccccgta gaaagatca aaggatcttc ttgagatcct ttttttctgc gcgtaatctg     780
ctgcttgcaa acaaaaaaac caccgctacc agcggtggtt tgtttgccgg atcaagagct   840
accaactctt tttccgaagg taactggctt cagcagagcg cagataccaa atactgtcct   900
tctagtgtag ccgtagttag gccaccactt caagaactct gtagcaccgc ctacatacct  960
cgctctgc                                                             968
```

<210> SEQ ID NO 5
<211> LENGTH: 2246
<212> TYPE: DNA
<213> ORGANISM: Artificial Sequence
<220> FEATURE:
<223> OTHER INFORMATION: Description of Artificial Sequence: Synthetic plasmid pKF3 sequence

<400> SEQUENCE: 5

```
atggcaacag tcaatcagct ggttcgaaag ccgcgagctc gtaaagtggc caaatctaac      60
gttccggctc tcgaggcatg cccgtagaag cgtggcatat gcacacgcgt atacactact     120
actccgaaga aaccgaattc agcgctgcgc aagctttgcc gcgtacgcct gaccaacggt     180
ttcgaggtca cctcatatat aggtggtgaa ggacacaacc tgcaggaaca ctctgttatc    240
ctgatcagag gcggccgcgt taaagatctg cccgggatcc ggtaccacac cgtccgcggc    300
gctctagact gctccggagt aaaggaccgt cgacaggatc gatcgaaata cggtgtaaaa    360
cgtccgaagg cctaatagaa gctagcttgg cactgggcca agctgaattt ctgccattca    420
tccgcttatt atcacttatt caggcgtagc accaggcgtt taagggcacc ataactgcc     480 ttaaaaaaat tacgccccgc cctgccactc atcgcagtac tgttgtaatt cattaagcat     540
tctgccgaca tggaagccat cacagacggc atgatgaacc tgaatcgcca gcggcatcag    600
caccttgtcg ccttgcgtat aatatttgcc catagtgaaa acgggggcga agaagttgtc    660
catattagcc acgtttaaat caaaactggt gaaactcacc cagggattgg ctgagacgaa    720
aaacatattc tcaataaacc ctttagggaa ataggccagg ttttcaccgt aacacgccac    780
atcttgcgaa tatatgtgta gaaactgccg gaaatcgtcg tggtattcac tccagagcga    840
tgaaaacgtt tcagttttgct catggaaaac ggtgtaacaa gggtgaacac tatcccatat    900
caccagctca ccgtctttca ttgccatacg aaattccgta tgagcattca tcaggcgggc    960
aagaatgtga ataaaggccg gataaaactt gtgcttattt ttctttacgg tctttaaaaa   1020
ggccgtaata tccagatgaa cggtctggtt ataggtacat tgagcaactg actgaaatgc   1080
ctcaaaatgt tctttacgat gccattggga tatatcaacg gtggtatatc cagtgatttt   1140
tttctccatt ttagcttcct tagctcctga aaatctcgat aactcaaaaa atacgcccgg   1200
tagtgatctt atttcattat ggtgaaagtt ggaacctctt acgtgccgat caacgtctca   1260
ttttcgccaa aagttggccc agggcttccc ggtatcaaca gggacaccag gatttattta   1320
ttctgcgaag tgatcttccg ttcgacggag ttccactgag cgtcagaccc cgtagaaaag   1380
```

```
atcaaaggat cttcttgaga tccttttttt ctgcgcgtaa tctgctgctt gcaaacaaaa    1440
aaaccaccgc taccagcggt ggtttgtttg ccggatcaag agctaccaac tcttttttccg   1500 aaggtaactg gcttcagcag agcgcagata ccaaatactg tccttctagt gtagccgtag    1560
ttaggccacc acttcaagaa ctctgtagca ccgcctacat acctcgctct gctaatcctg    1620
ttaccagtgg ctgctgccag tggcgataag tcgtgtctta ccggttgga ctcaagacga     1680 tagttaccgg ataaggcgca gcggtcgggc tgaacggggg gttcgtgcac acagcccagc    1740
ttggagcgaa cgacctacac cgaactgaga tacctacagc gtgagcattg agaaagcgcc    1800
acgcttcccg aagggagaaa ggcggacagg tatccgtaa gcggcagggt cggaacagga     1860
gagcgcacga gggagcttcc aggggggaaac gcctggtatc tttatagtcc tgtcgggttt    1920
cgccacctct gacttgagcg tcgattttg tgatgctcgt caggggggcg gagcctatgg     1980
aaaaacgcca gcaacgcggc cttttttacgg ttcctggcct tttgctggcc ttttgctcac    2040
atgttctttc ctgcgttatc ccctgattct gtggataacc gtattaccgc ctttgagtga    2100
gctgataccg ctcgccgcag ccgaacgacc gagcgcagcg agtcagtgag cgaggaagcg    2160
gaagaagcat tctgaaatga gctgttgaca attaatcatc gaactagtta actagtacgc    2220
aagttcacgt aaaagggta tcgacc                                         2246

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      plasmid pKF3 sequence

<400> SEQUENCE: 6
tttttttttt acattttgag gcatttcagt                                     30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      plasmid pKF3 sequence

<400> SEQUENCE: 7
tttttttttt acattttgag acatttcagt                                     30
```